United States Patent [19]
Polli et al.

[11] 3,974,272
[45] Aug. 10, 1976

[54] PALATABLE CHOLESTYRAMINE COACERVATE COMPOSITIONS

[75] Inventors: Gerald P. Polli, Somerville, N.J.; Clyde E. Shoop, Lansdale, Pa.

[73] Assignee: Merck & Co., Inc., Rahway, N.J.

[22] Filed: Jan. 25, 1974

[21] Appl. No.: 436,420

Related U.S. Application Data

[63] Continuation-in-part of Ser. No. 285,719, Sept. 1, 1972, abandoned.

[52] U.S. Cl.................................. 424/78; 424/361; 424/362
[51] Int. Cl.² ................ A61K 31/785; A61K 47/00
[58] Field of Search...................... 424/78, 35, 362

[56] References Cited
UNITED STATES PATENTS

| | | | |
|---|---|---|---|
| 2,701,782 | 2/1955 | Culter | 424/362 |
| 3,251,824 | 5/1966 | Battista | 424/362 |
| 3,499,960 | 3/1970 | Macek et al. | 424/33 |

OTHER PUBLICATIONS

Moore et al. — Chem. Abst. vol. 69 (1968) p. 50833u.

*Primary Examiner*—Sam Rosen
*Attorney, Agent, or Firm*—Rudolph J. Anderson; Harry E. Westlake; Frank M. Mahon

[57] ABSTRACT

Palatable oral coacervate compositions containing Cholestyramine and a Modified Gum selected from the group consisting of hydrophilic colloid of cellulosive material and charged anionic gum in an aqueous medium.

20 Claims, No Drawings

PALATABLE CHOLESTYRAMINE COACERVATE COMPOSITIONS

This application is a continuation-in-part of our pending application Ser. No. 285 719 filed Sept. 1, 1972, now abandoned.

This invention relates to the preparation of palatable compositions which contain Cholestyramine and a Modified Gum selected from the group consisting of hydrophilic colloid of cellulosive material and charged anionic gum. More specifically, the invention relates to the preparation of palatable coacervate compositions containing Cholestyramine and a Modified Gum selected from the group consisting of hydrophilic colloid of cellulosive material and charged anionic gum in an aqueous medium. The pharmaceutical compositions included herein are useful in the treatment of hypocholesteremia and biliary cirrhosis.

Hypocholesteremia which is also known as high blood cholesterol level, is believed to be responsible in many cases for atherosclerosis. Therefore, it is exceedingly desirable to effect a reduction of the blood cholesterol level in atherosclerosis patients. This has been done heretofore primarily through the use of low fat diets. However, in many patients this is not sufficient to maintain the cholesterol with the desired limits. Accordingly, it is desirable to administer to the patient a hypocholesteremic agent.

In biliary cirrhosis or other forms of bile stasis, pruritis, a severe itching especially at the anus, is a major complaint of patients suffering from interference with normal excretion of bile. Accordingly, it is desired to administer an anti-pruritic agent to the patient.

It has been known that in the preparation of Cholestyramine oral form compositions, astrigent, difficult to swallow and other undesirable conditions may result due to the chemical and physical properties of Cholestyramine. The prior art teaches the preparation of palatable compositions which contain polystyrene-divinyl-benzene copolymer anion exchange resin (Cholestyramine) and acrylic polymer cross-linked with allyl-sucrose as a coating agent (Carbopol 934). For example, see U.S. Pat. No. 3,499,960 and Merck Index, 8th Edition, page 253 (1968).

It is an object of this invention to prepare a palatable composition which contains cholestyramine.

It is a further object of this invention to prepare a palatable composition which contains a coacervate which possesses small palatable digestable flocs from Cholestyramine and a Modified Gum selected from the group consisting of hydrophilic colloid or cellulosive material and charged anionic gum in an aqueous material medium.

Another object of this invention is the preparation of a palatable composition which contains cholestyramine in an enhanced palatable condition.

In accordance with this invention, it is found that a Modified Gum selected from the group consisting of hydrophilic colloid of cellulosive material and charged anionic gum produces a coacervate with Cholestyramine in an aqueous medium. Also, it is found that the Cholestyramine coacervate disclosed herein which is in the form of small palatable digestable flocs overcomes the gritty astrigent taste of Cholestyramine. The Cholestyramine coacervate compositions disclosed herein possess palatability, non-astringent and ease to swallow properties.

In order to ensure that Cholestyramine is encompassed within the composition of this invention in the coacervate form it is necessary to employ a Modified Gum which will form a coacervate with Cholestyramine in an aqueous medium. The composition employed in the practice of this invention which contains the active ingredient in a coacervate form may be prepared according to any method known to the art for the manufacture of pharmaceutical compositions. The essential ingredients of the compositions employed herein are Cholestyramine and a Modified Gum selected from the group consisting of hydrophilic colloid of cellulosive material and charged anionic gum in an aqueous medium.

Representative Modified Gum which can be employed in this invention includes hydrophilic colloid of cellulosive materials such as methylcellulose, ethylcellulose, sodium carboxymethyl cellulose, hydroxyethyl cellulose and hydroxypropyl cellulose and charged anionic gums such as carrageenan, sodium alginate, potassium alginate and propylene glycol alginate. Of particular preference is sodium carboxymethyl cellulose or sodium alginate.

Representative aqueous mediums which can be employed in the practice of this invention are water, milk, and fruit juices such as orange, grapefruit, tomato, pineapple and the like.

Optionally, either a water-insoluble or soluble dispersing agent may be employed in the practice of this invention. When employed, representative water-insoluble dispersing agents are corn starch, dibasic calcium phosphate and potato starch and representative water soluble dispersing agents are Primojel (Edward Mendel Company, Inc. Technical Bulletin, 1970), sucrose and dextrose. Of particular preference is Primojel or corn starch.

Primojel is a low-substituted carboxymethyl-starch which dissolves very rapidly in water, possesses superior disintegrating ability and is represented by the formula below:

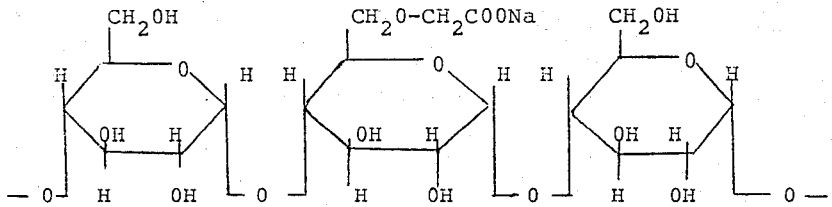

wherein the degree of substitution (DS) is about 0.25, this meaning that per 100 glucose units, approximately 25 carboxymethyl groups have been introduced. The glucopyranose units in starch are connected to each other by alpha-glucosidic linkages. It is a fine, white, flowable powder having a pH of 7.0–7.5 (in a 2% solution in distilled water) and an ash content of approximately 15% consisting of sodium chloride (approximately 5%) and sodium carbonate which is from the carboxyl groups.

The pharmaceutical compositions of this invention contain Cholestyramine and a Modified Gum selected from the group consisting of hydrophilic colloid of cellulosive material and charged anionic gum in an aqueous medium. To each part by weight of Modified Gum is combined from about 4 to 10 parts by weight of cholestyramine and from about 4 to 10 oz. of aqueous medium. Of particular preference is a combination of 1 part Modified Gum, from about 6 to 8 parts cholestyramine and from about 5 to 8 oz. of aqueous medium. Optionally, a water-insoluble or soluble dispersing agent can be added to the composition at about 0.5 to 1.5 parts per part by weight of Modified Gum. Of particular preference is a combination of about 8 to 10 parts by weight cholestyramine, about 0.8 to 1.3 parts by weight of water-insoluble or soluble dispersing agent and from about 5 to 8 oz. aqueous medium per part by weight of Modified Gum.

It should be noted furthermore that the palatable Cholestyramine coacervate compositions disclosed herein are orally administered according to the same as heretofore. Of particular preference is the administration of a composition containing about 40.0 to 80.0 mg./kg. of body weight by weight of Cholestyramine for varying periods of treatment as required, preferable three times a day. The formulations included herein are effective in the treatment of hypocholesteremia and biliary cirrhosis conditions in patients.

The Cholestyramine in the coacervate compositions disclosed herein when taken internally by patients becomes readily available to the body as hypocholesteremic and anti-pruritic agents.

It will be understood, however, that the specific dose level for any particular patient will depend upon a variety of factors including the age, body weight, general health, sex, diet, time of administration, rate of excretion, drug combination and the severity of the particular disease undergoing therapy.

The following examples illustrate the preparation of the various palatable Cholestyramine-coacervate compositions of the invention. The examples should be construed as an illustration of the invention rather than limitation.

The dry regents, Cholestyramine, sodium carboxymethyl cellulose, Primojel and lactose are mixed throughly into a powdered blend. An aliquot sample from the dry mixture is removed, mixed with flavor and then re-mixed with the original blend. The resulting powder blend mixture is then passed through a No. 80 mesh screen. The palatable cholestyramine-coacervate composition is obtained when mixed with 4 to 10 oz. of aqueous medium. Of preference is a cholestyramine-coacervate composition containing 5.0 grams of the palatable powder composition mixed with approximately 6 oz. of aqueous medium prior to administration. Representative aqueous medium which can be employed in this invention are water, milk and fruit juices such as orange, grapefruit, tomato, pineapple and the like.

Other Modified Gums such as methyl cellulose, ethyl cellulose, hydroxyethyl cellulose, hydroxypropyl cellulose, carrageenan, sodium alginate, potassium alginate or propylene glycol alginate can be substituted for sodium carboxymethyl cellulose, and other water soluble or insoluble dispersing agents such as corn starch, dibasic calcium phosphate, sucrose, potato starch or dextrose can be substituted for Primojel.

Table II

| Ingredients(g) | Ex.1 | Ex.2 | Ex.3 | Ex.4 | Ex.5 | Ex.6 | Ex.7 | Ex.8 |
| --- | --- | --- | --- | --- | --- | --- | --- | --- |
| Cholestyramine | 3.75 | 3.63 | 3.67 | 3.50 | 4.00 | 3.25 | 4.00 | 3.75 |
| Sodium Carboxymethyl celluose | .40 | .45 | .50 | .45 | .45 | .65 | .40 | .75 |
| Lactose and flavor, q.s. | | | | | | | | |
| Total Weight (g) | 5.0 | 5.0 | 5.0 | 5.0 | 5.0 | 5.0 | 5.0 | 5.0 |

The dry reagents, Cholestyramine, sodium carboxymethyl cellulose and lactose are mixed throughly into a powdered blend. An aliquot sample from the dry mixture is removed, mixed with flavor and then re-mixed with the original blend. The resulting powder blend mixture is then passed through a No. 80 mesh screen. The palatable cholestyramine-coacervate composition is obtained when mixed with 4 to 10 oz. of aqueous medium. Of preference is a Cholestyramine-coacervate composition containing 5.0 grams of the palatable powder composition mixed with approximately 6 oz. of aqueous medium prior to administration. Representative aqueous mediums which can be employed in this invention are water, milk and fruit juices such as orange, grapefruit, tomato, pineapple and the like.

Other Modified Gums such as methyl cellulose, ethyl cellulose, hydroxyethyl cellulose, hydroxypropyl cellulose, carrageenan, sodium alginate, potassium alginate or propylene glycol alginate can be substituted for sodium carboxymethyl cellulose.

Table I

| Ingredients(g) | Ex.1 | Ex.2 | Ex.3 | Ex.4 | Ex.5 | Ex.6 | Ex.7 | Ex.8 |
| --- | --- | --- | --- | --- | --- | --- | --- | --- |
| Cholestyramine | 3.75 | 3.63 | 3.67 | 3.50 | 4.00 | 3.25 | 4.00 | 3.75 |
| Sodium Carboxymethyl celluose | .40 | .45 | .50 | .45 | .45 | .65 | .40 | .75 |
| Primojel | .50 | .50 | .40 | .55 | .40 | .75 | .50 | .40 |
| Lactose and flavor, q.s | | | | | | | | |
| Total Weight (g) | 5.0 | 5.0 | 5.0 | 5.0 | 5.0 | 5.0 | 5.0 | 5.0 |

Table III

| Ingredients(g) | Ex.1 | Ex.2 | Ex.3 | Ex.4 | Ex.5 | Ex.6 | Ex.7 | Ex.8 |
|---|---|---|---|---|---|---|---|---|
| Cholestyramine | 3.75 | 3.63 | 3.67 | 3.50 | 4.00 | 3.25 | 4.00 | 3.75 |
| Sodium Carboxymethyl cellulose | .40 | .45 | .50 | .45 | .45 | .65 | .40 | .75 |
| Corn Starch | .50 | .50 | .40 | .55 | .40 | .75 | .50 | .40 |
| Lactose and Flavor, q.s. | | | | | | | | |
| Total Weight (g) | 5.0 | 5.0 | 5.0 | 5.0 | 5.0 | 5.0 | 5.0 | 5.0 |

The dry reagents, Cholestyramine, sodium carboxymethyl cellulose, corn starch and lactose are mixed throughly into a powder blend. An aliquot sample from the dry mixture is removed, mixed with flavor and then re-mixed with the original blend. The resulting powder blend mixture is then passed through a No. 80 mesh screen. The palatable cholestyramine-coacervate composition is obtained when mixed with 4 to 10 oz. of aqueous medium. Of preference is a Cholestyramine-coacervate composition containing 5.0 grams of the palatable powder composition mixed with approximately 6 oz. of aqueous medium prior to administration. Representative aqueous mediums which can be employed in this invention are water, milk and fruit juices such as orange, grapefruit, tomato, pineapple and the like.

Other Modified Gums such as methyl cellulose, ethyl cellulose, hydroxyethyl cellulose, hydroxypropyl cellulose, carrageenan, sodium alginate, potassium alginate or propylene glycol alginate can be substituted for sodium carboxymethyl cellulose, and other water soluble or insoluble dispersing agents such as Primojel, dibasic calcium phosphate or potato starch can be substituted for corn starch.

What is claimed is:

1. An oral palatable composition comprising an aqueous medium selected from the group consisting of water, milk and fruit juice; a modified gum selected from the group consisting of hydrophilic colloid of cellulosive material and charged anionic gum wherein the hydrophilic colloid of cellulosive material is selected from the group consisting of methyl cellulose, ethyl cellulose, sodium carboxymethyl cellulose, hydroxy ethyl cellulose and hydroxypropyl cellulose and the charged anionic gum is selected from the group consisting of carageenan, sodium alginate, potassium alginate and propylene glycol alginate; and an effective amount of cholestyramine, wherein there is present from about 4 to 10 parts of cholestyramine and from about 4 to 10 oz. of the aqueous medium per part of modified gum to the total weight of the formulation and wherein the cholestyramine and the modified gum, in the presence of the aqueous medium, are in coacervate form.

2. The composition of claim 1 wherein there is present 6 to 8 parts of cholestyramine and 5 to 8 oz. aqueous medium per part of modified gum.

3. The composition of claim 2 wherein the modified gum is hydrophilic colloid of cellulosive material and the aqueous medium is a fruit juice.

4. The composition of claim 3 wherein the hydrophilic colloid of cellulosive material is sodium carboxymethyl cellulose and the aqueous medium is a fruit juice selected from the group consisting of orange juice, grapefruit juice, tomato juice and pineapple juice.

5. The composition of claim 1 further comprising a water soluble dispersing agent selected from the group consisting of sucrose, dextrose and a low substituted carboxymethyl starch of the formula:

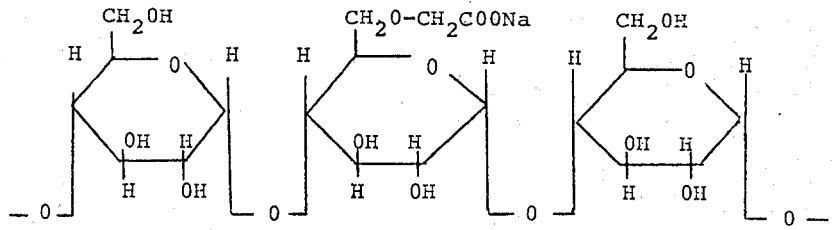

which ranges from 0.5 to 1.5 parts per part of modified gum.

6. The composition of claim 5 wherein the water soluble dispersing agent is a low substituted carboxymethyl starch and the modified gum is hydrophilic colloid of cellulosive material and the aqueous medium is a fruit juice.

7. The composition of claim 6 wherein the hydrophilic colloid of cellulosive material is sodium carboxymethyl cellulose.

8. The composition of claim 1 further comprising a water insoluble dispersing agent selected from the group consisting of corn starch, dibasic calcium phosphate and potato starch which ranges from 0.5 to 1.5 parts per part of modified gum.

9. The composition of claim 8 wherein the water insoluble dispersing agent is corn starch, the modified gum is hydrophilic colloid of cellulosive material and the aqueous medium is a fruit juice.

10. The composition of claim 9 wherein the hydrophilic colloid of cellulosive material is sodium carboxymethyl cellulose.

11. A method of treating a patient suffering from a condition exhibiting at least one of the symptoms of hypocholesteremia and biliary cirrhosis which comprises oral administration of a composition comprising an aqueous medium selected from the group consisting of water, milk, and fruit juice; a modified gum selected from the group consisting of hydrophilic colloid of cellulosive material and charged anionic gum wherein the hydrophilic colloid of cellulosive material is selected from the group consisting of methyl cellulose,

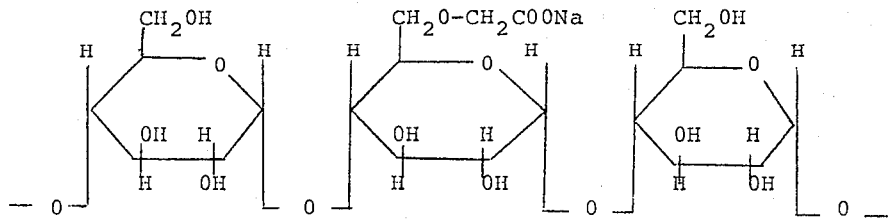

ethyl cellulose, sodium carboxymethyl cellulose, hydroxyethyl cellulose and hydroxypropyl cellulose and the charged anionic gum is selected from the group consisting of carrageenan, sodium alginate, potassium alginate and propylene glycol alginate; and an effective amount of cholestyramine, wherein there is present from about 4 to 10 parts of cholestyramine and from about 4 to 10 oz. of aqueous medium per part of modified gum to the total weight of the formulation and wherein the cholestyramine and the modified gum, in the presence of the aqueous medium, are in coacervate form.

12. The method of claim 11 wherein there is present 6 to 8 parts of cholestyramine and 5 to 8 oz. aqueous medium per part of modified gum.

13. The method of claim 12 wherein the modified gum is hydrophilic colloid of cellulosive material and the aqueous medium is a fruit juice.

14. The method of claim 13 wherein the hydrophilic colloid of cellulosive material is sodium carboxymethyl cellulose and the aqueous medium is a fruit juice selected from the group consisting of orange juice, grapefruit juice, tomato juice and pineapple juice.

15. The method of claim 11 further comprising a water soluble dispersing agent selected from the group consisting of sucrose, dextrose and a low substituted carboxymethyl starch of the formula: which ranges from 0.5 to 1.5 part per part of modified gum.

16. The method of claim 15 wherein the water soluble dispersing agent is a low substituted carboxymethyl starch, the modified gum is hydrophilic colloid of cellulosive material and the aqueous medium is a fruit juice.

17. The method of claim 16 wherein the hydrophilic colloid of cellulosive material is sodium carboxymethyl cellulose.

18. The method of claim 11 further comprising a water insoluble dispersing agent selected from the group consisting of corn starch, dibasic calcium phosphate and potato starch which ranges from 0.5 to 1.5 part per part of modified gum.

19. The method of claim 18 wherein the water insoluble dispersing agent is corn starch, the modified gum is hydrophilic colloid of cellulosive material and the aqueous medium is a fruit juice.

20. The method of claim 19 wherein the hydrophilic colloid of cellulosive material is sodium carboxymethyl cellulose.

* * * * *